(12) United States Patent
Gorrotxategi Salaberria

(10) Patent No.: US 10,379,378 B2
(45) Date of Patent: Aug. 13, 2019

(54) PROGRESSIVE OPHTHALMIC LENSES

(71) Applicant: OPTOMETRIC AIR LENS. S.L., San Sebastian (ES)

(72) Inventor: Joseba Gorrotxategi Salaberria, San Sebastian (ES)

(73) Assignee: OPTOMETRIC AIR LENS, S.L., San Sebastian (ES)

( * ) Notice: Subject to any disclaimer, the term of this patent is extended or adjusted under 35 U.S.C. 154(b) by 189 days.

(21) Appl. No.: 15/324,253

(22) PCT Filed: Jul. 8, 2015

(86) PCT No.: PCT/EP2015/065575
§ 371 (c)(1),
(2) Date: Jan. 5, 2017

(87) PCT Pub. No.: WO2016/005437
PCT Pub. Date: Jan. 14, 2016

(65) Prior Publication Data
US 2017/0199394 A1    Jul. 13, 2017

(30) Foreign Application Priority Data
Jul. 9, 2014   (ES) .................................. 201431028

(51) Int. Cl.
*G02C 7/02*      (2006.01)
*A61B 3/11*      (2006.01)
*G02C 7/06*      (2006.01)

(52) U.S. Cl.
CPC .............. *G02C 7/027* (2013.01); *A61B 3/111* (2013.01); *G02C 7/028* (2013.01); *G02C 7/068* (2013.01)

(58) Field of Classification Search
CPC .......... G02C 7/02; G02C 7/024; G02C 7/027; G02C 7/028
See application file for complete search history.

(56) References Cited

U.S. PATENT DOCUMENTS

| | | |
|---|---|---|
| 2010/0141893 A1 | 6/2010 | Altheimer et al. |
| 2011/0184830 A1 | 7/2011 | Guilloux et al. |
| 2012/0008090 A1 | 1/2012 | Helmut Altheimer et al. |
| | | (Continued) |

OTHER PUBLICATIONS

International Search Report and Written Opinion of the International Searching Authority dated Oct. 5, 2015 for PCT/EP2015/065575, 10 pages.

*Primary Examiner* — William R Alexander
*Assistant Examiner* — Ephrem Z Mebrahtu
(74) *Attorney, Agent, or Firm* — Squire Patton Boggs (US) LLP

(57) ABSTRACT

Methods of designing at least one progressive ophthalmic lens for a user having a dominant eye and a non-dominant eye are provided. These methods include determining a first inset for a lens for the dominant eye, and determining a measurement of phoria of the user. The methods further include determining a second inset for a lens for the non-dominant eye depending on the first inset and on the measurement of phoria, and designing the lens for the non-dominant eye according to the second inset. Systems, computer systems and computer program products suitable for performing these design methods are also provided. Progressive ophthalmic lenses designed according to said design methods are also provided.

17 Claims, 4 Drawing Sheets

(56) References Cited

U.S. PATENT DOCUMENTS

2013/0329186 A1\* 12/2013 Contet .................. G02C 7/028
                                                        351/159.77
2015/0124214 A1\*  5/2015 Contet .................. G02C 7/027
                                                        351/204

\* cited by examiner

PROGRESSIVE OPHTHALMIC LENSES

The present invention relates to a method of designing at least one progressive ophthalmic lens, and to a system, computer system and computer program product suitable for carrying out said design method.

The present invention also relates to a progressive ophthalmic lens designed according to said design method.

BACKGROUND ART

Ophthalmic lenses may be prescribed to a user having at least one power corresponding to what the user needs to compensate for certain visual defects, of either positive or negative strength. An example of such visual defects may be astigmatism. Ophthalmic lenses may be adapted in a glasses frame depending on the prescribed power and the relative position of the user's eyes with respect to the glasses frame (vertex distance).

For presbyopic people (users with eyestrain), lenses may be prescribed with different powers (for near vision and far vision), given the difficulty of accommodation that this type of users usually have. In these progressive lenses, a power may be defined at the top of the lens corresponding to far vision, with a progressive increase of downward addition up to achieve a power for near vision at the bottom of the lens.

Optometry may be defined as the science responsible for the primary care of the visual health through actions of prevention, diagnosis, treatment and correction of defects.

In order to determine the most appropriate characteristics for glasses and, in particular, for the progressive lenses of the glasses, the user that will wear the glasses is usually subjected to an optometric study. This study may be performed using different techniques and devices aimed at that purpose, and may result in various optometric parameters associated with the user.

Typical examples of such optometric parameters may be: power for near and far vision, near and far inter-pupillary distance, working distance (which may take into account the prescribed power for near vision), vertex distance for a particular glasses frame, identification of the dominant eye, etc.

Normally a person has a dominant eye and a non-dominant eye. The dominant eye is the eye that has a greater visual acuity and, therefore, dominates the depth vision. The non-dominant eye usually dominates the peripheral and spatial vision. Their interaction causes the brain to receive a three-dimensional image. Usually the dominant eye is the eye that is used to look through a microscope, a camera, or for any task in which only one eye is used.

The parameter relating to the near inter-pupillary distance may be defined as the measurement of the distance between the centers of the pupils of the user when the user is looking at an object that is located at a position near to the eyes of the user.

The parameter relating to the far inter-pupillary distance may be defined as the measurement of the distance between the centers of the pupils of the user when the user is looking at an object that is located at a far position from the eyes of the user.

The parameter relating to the working distance (which may take into account a prescribed power for near vision) may be defined as the distance between the user's eyes and a working area which is habitual/comfortable for the user, such as for example a reading distance.

The parameter relating to the vertex distance (for a given glasses frame) may be defined as the measurement of the distance between the front surface of the eye and the rear surface of the lens mounted on the glasses frame.

All these optometric parameters are widely known and used in the field of optometry, and are often based on standards which make their values to be substantially unambiguously interpreted by the optometric technicians.

In progressive lenses, the position of the power for near vision with respect to the power for far vision in its horizontal displacement is called inset. In conventional progressive lenses, the inset usually has a fixed value accepted as standard. Some of these insets may cause a number of limitations for the ocular convergence in terms of, for example, the working distance and the value of the prescription (power).

Therefore, many users may have difficulties of adaptation to progressive lenses even in the case of having a normal binocular vision and possibly other normal clinical parameters. Clinical cases that may indicate a failure to adapt to progressive lenses may include: strabismus, amblyopia, anisometropia, convergence dysfunction, retinal pathologies, etc.

SUMMARY

Therefore, there is a need for new methods, systems, computer systems and computer program products for designing at least one progressive ophthalmic lens, and for a new progressive ophthalmic lens, improving user adaptation to such a type of lenses.

In a first aspect, a method of designing at least one progressive ophthalmic lens for a user having a dominant eye and a non-dominant eye is provided. The method comprises determining a first inset for a lens for the dominant eye, determining a measurement of phoria of the user, and determining a second inset for a lens for the non-dominant eye depending on the first inset and on the measurement of phoria of the user. The method further comprises designing the lens for the non-dominant eye according to the second inset.

Phoria may be defined as a latent deviation of the visual axes that may occur in the absence of visual stimuli. It may be the state defined by the rotational position of the eyes in binocular vision in which the fusion of images is broken. It may be a state of relaxation induced voluntarily or through some artifice, in which every eye momentarily loses its coordination with the other, keeping the visual stimulus but without any integration in the brain.

Determining the second inset for the lens of the non-dominant eye depending on the phoria and on the first inset (for the lens of the dominant eye) allows a design more beneficial to the user. Specifically, this second inset (dependent on the phoria and on the first inset for the lens of the dominant eye) may cause the user not to have to move his/her fixation with an excessive demand for fusional reserves. Therefore, the risk for the user to suffer visual defects due to a poor adaptation to the lenses is reduced.

Determining the first inset for the lens of the dominant eye may be performed through different known optometric techniques/devices. In some examples, determining the first inset for the lens of the dominant eye may comprise determining said first inset with a fixed value of between 2 and 3 mm, more preferably 2.5 mm. Other ways to determine the first inset for the lens of the dominant eye will be described hereinafter.

Once the first inset for the lens of the dominant eye has been determined, the second inset for the lens of the non-dominant eye may be determined from the first inset (for the lens of the dominant eye) and a measurement of phoria (for the non-dominant eye). This measurement of phoria may be determined in various ways based on known techniques/devices of optometric examination of the user aimed at that purpose.

In the context of the proposed method, determining the measurement of phoria may comprise, for example, its retrieval from a data base of optometric data of the patient, provision of the corresponding value to the method by an optometrist (or another appropriate person), etc. This provision of the phoria by the optometrist may be performed through any known means of data entry, such as for example a keyboard, a touch screen, etc.

Once the first inset for the lens of the dominant eye and the second inset for the lens of the non-dominant eye have been obtained, one or more further aspects of the design of the lenses may be determined by any known technique in order to complete the design of the lenses.

According to some examples, the method may further comprise determining a measurement of far inter-pupillary distance for the user, a measurement of near inter-pupillary distance for the user, a measurement of working distance for the user, and a measurement of vertex distance for the user. The measurement of the working distance may be determined depending on a power for near vision prescribed to the user. The measurement of the vertex distance may be determined depending on a glasses frame selected for the user. Thus, the first inset for the lens for the dominant eye may be determined depending on said measurements of far inter-pupillary distance and near inter-pupillary distance, working distance and vertex distance.

Specifically, the first inset for the lens of the dominant eye may be determined according to the following formula:

$$\text{inset\_dom} = \frac{FIPD}{2} - \frac{WD - VD}{WD/(NIPD/2)} \qquad \text{Formula 1}$$

wherein:
inset_dom is the first inset for the lens of the dominant eye,
FIPD is the measurement of the far inter-pupillary distance,
NIPD is the measurement of the near inter-pupillary distance,
WD is the measurement of the working distance depending on the prescribed power for near vision, and
VD is the measurement of the vertex distance.

Formula 1 may be derived from a suitable mathematical model as it will be described hereinafter. This Formula 1 constitutes an alternative way to determine the first inset for the lens of the dominant eye with respect to the attribution of a fixed value (for example 2.5 mm) as previously discussed.

The far inter-pupillary distance (FIPD in Formula 1) and the near inter-pupillary distance (NIPD in Formula 1), the working distance (WD in Formula 1) and the vertex distance (VD in Formula 1) may have been previously obtained through an optometric examination of the user. This examination may have been performed according to any known optometric technique.

In the context of some examples, determining the far inter-pupillary distance (FIPD) and the near inter-pupillary distance (NIPD), the working distance (WD) and the vertex distance (VD) may comprise, for example, their retrieval from a data base of optometric data of the user, their provision to the design method by an optometrist (using for example a keyboard, touch screen . . . ) and so on.

In some examples, the second inset for the lens of the non-dominant eye may be determined according to the following formula:

$$\text{inset\_nondom} = \text{inset\_dom} - \frac{Ph \times 10}{1000} \times 12 \qquad \text{Formula 2}$$

wherein:
inset_nondom is the second inset for the lens of the non-dominant eye of the user,
inset_dom is the first inset for the lens of the dominant eye of the user, and
Ph is the measurement of phoria of the user.

Formula 2 may be derived from a suitable mathematical model as it will be described hereinafter.

Alternatively to the examples based on Formula 2, the method may further comprise determining a measurement of near inter-pupillary distance, a measurement of working distance and a measurement of vertex distance. Thus, the second inset for the lens of the non-dominant eye may be determined further depending on these measurements. The measurement of the working distance may be determined depending on a power for near vision prescribed to the user, and the measurement of the vertex distance may be determined depending on a glasses frame selected for the user.

These measurements of near inter-pupillary distance, working distance and vertex distance may be the same measurements of near inter-pupillary distance, working distance and vertex distance previously mentioned in relation to examples using these measurements for determining the first inset for the lens of the dominant eye (through, for example, Formula 1). In these particular cases, the determination only once of each of these measurements would suffice to determine both the first inset (for the lens of the dominant eye) and the second inset (for the lens of the non-dominant eye).

In some examples, the determination of the second inset (for the lens of the non-dominant eye) depending on the first inset (for the lens of the dominant eye) and on the measurements of phoria, near inter-pupillary distance, working distance and vertex distance may be performed according to the following formula:

$$\text{inset\_nondom} = \text{inset\_dom} - \frac{\frac{Ph \times (VD/\sin(\arctg(WD/(NIPD/2))))}{1000}}{\cos(90 - \arctg(WD/(NIPD/2)))} \qquad \text{Formula 3}$$

wherein:
inset_nondom is the second inset for the lens of the non-dominant eye,
inset_dom is the first inset for the lens of the dominant eye,
NIPD is the measurement of the near inter-pupillary distance,
WD is the measurement of the working distance depending on the prescribed power for near vision,
VD is the measurement of the vertex distance, and
Ph is the measurement of the phoria of the user.

Formula 3 may be derived from a suitable mathematical model as it will be described hereinafter.

According to some examples, the design method may further comprise designing the lens for the dominant eye according to the first inset.

In some examples, a method of manufacturing at least one progressive ophthalmic lens may also be provided. This manufacturing method may comprise designing the at least one progressive ophthalmic lens by performing any one of the previous design methods. This manufacturing method may further comprise manufacturing the at least one progressive ophthalmic lens according to the result of designing the at least one progressive ophthalmic lens.

In a second aspect, a system is provided for designing at least one progressive ophthalmic lens for a user having a dominant eye and a non-dominant eye. This system comprises computer/electronic means for determining a first inset for a lens for the dominant eye, and computer/electronic means for determining a measurement of phoria of the user. This system further comprises computer/electronic means for determining a second inset for a lens for the non-dominant eye depending on the first inset and on the measurement of phoria, and computer/electronic means for designing the lens for the non-dominant eye according to the second inset.

In some examples, the system for designing at least one progressive ophthalmic lens may further comprise computer/electronic means for designing the lens for the dominant eye according to the first inset.

In a third aspect, a computer system is provided comprising a memory and a processor, wherein the memory stores computer program instructions that are executable by the processor, said instructions comprising functionalities to perform any one of the previous design methods.

In a fourth aspect, the invention provides a computer program product comprising program instructions for causing a (computer) system to execute any one of the previous design methods.

Such a computer program may be stored in a physical storage media, such as a recording means, a computer memory, or a read only memory, or may be carried by a carrier wave, such as an electrical or optical wave.

In a fifth aspect, a progressive ophthalmic lens is provided for a non-dominant eye of a user further having a dominant eye, designed according to any one of the previous design methods. Therefore, this lens for the non-dominant eye has a second inset depending on a first inset for a lens for the dominant eye and on a measurement of phoria of the user.

In some examples, a set of progressive ophthalmic lenses for glasses is provided. This set of lenses comprises the previous lens for the non-dominant eye, and the lens for the dominant eye having the mentioned first inset.

BRIEF DESCRIPTION OF THE DRAWINGS

Particular embodiments of the present invention will be described by way of non-limiting example with reference to the accompanying drawings, wherein.

DETAILED DESCRIPTION OF EMBODIMENTS

Specific details of the invention will be described in the following in order to provide a thorough understanding of the invention. However, a person skilled in the art should understand that the present invention may be practiced without some or all of these specific details. Moreover, certain well-known elements have not been described in detail in order to not unnecessarily complicate the description of the present invention.

Figure 1:
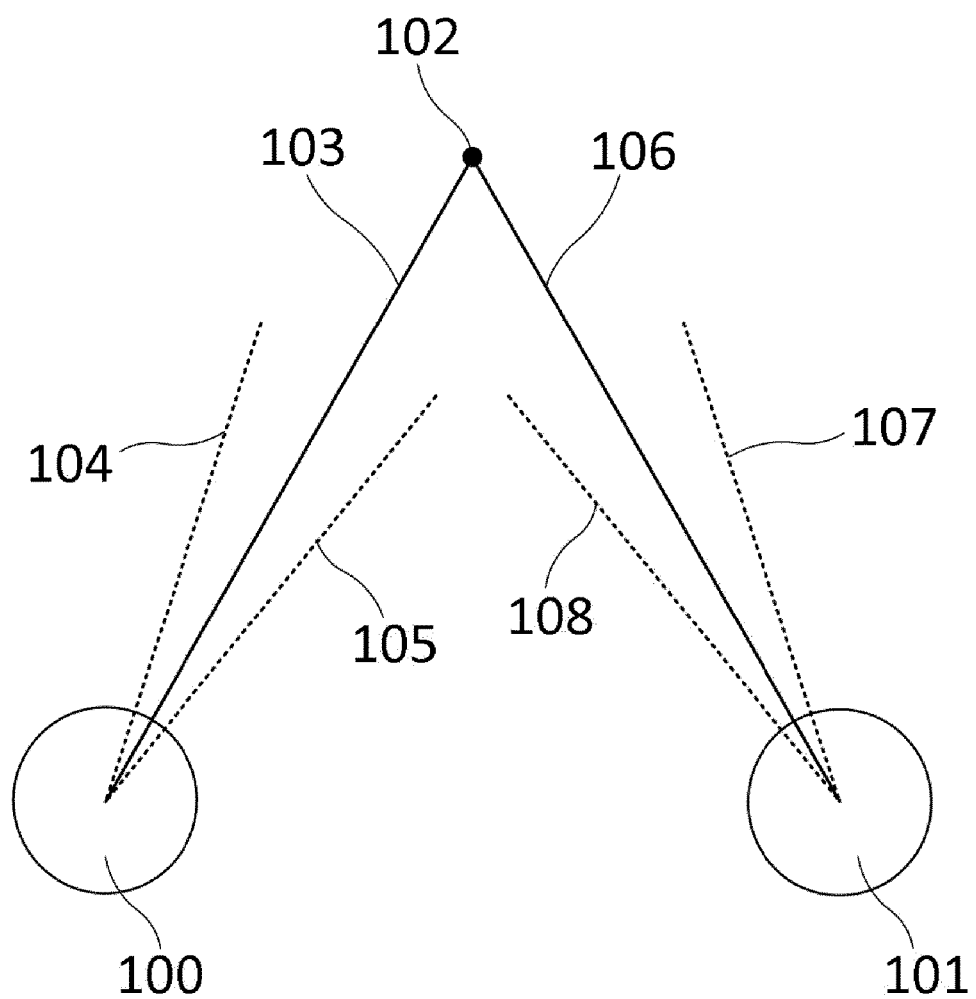
FIG. 1 shows a graphical representation of the eyes of a user and visual axes associated with said eyes.

In FIG. 1, a graphical representation of a right eye 101 and a left eye 100 of a person (user/patient) in near fixation is shown. A visual axis 103 for the left eye 100 according to a theoretical (near) fixation point 102 and a visual axis 106 for the right eye 101 according to the same theoretical fixation point 102 are shown.

Near fixation may be different depending on the user, depending on the value of phoria of the user. The visual axis 103 of the left eye 100 may move temporarily (towards the left temporal bone) or nasally (towards the nose) depending on the value of phoria of the user. The visual axis 106 of the right eye 101 may also move temporarily (to the right temporal bone) or nasally depending on the phoria of the user.

The type of phoria that causes a temporal movement (towards corresponding temporal bone) of the theoretical visual axis 103, 106 is called exophoria. In FIG. 1, a visual axis 104 for the left eye 100 caused by exophoria and a visual axis 107 for the right eye 101 also caused by exophoria are shown.

The type of phoria that may cause a nasal movement (towards the nose) of the theoretical visual axis 103, 106 is called esophoria. In FIG. 1, a visual axis 105 for the left eye 100 caused by esophoria and a visual axis 108 for the right eye 101 also caused by esophoria are shown.

The concepts of exophoria and esophoria will be used in other parts of the description in the context of various examples.

Figure 2:
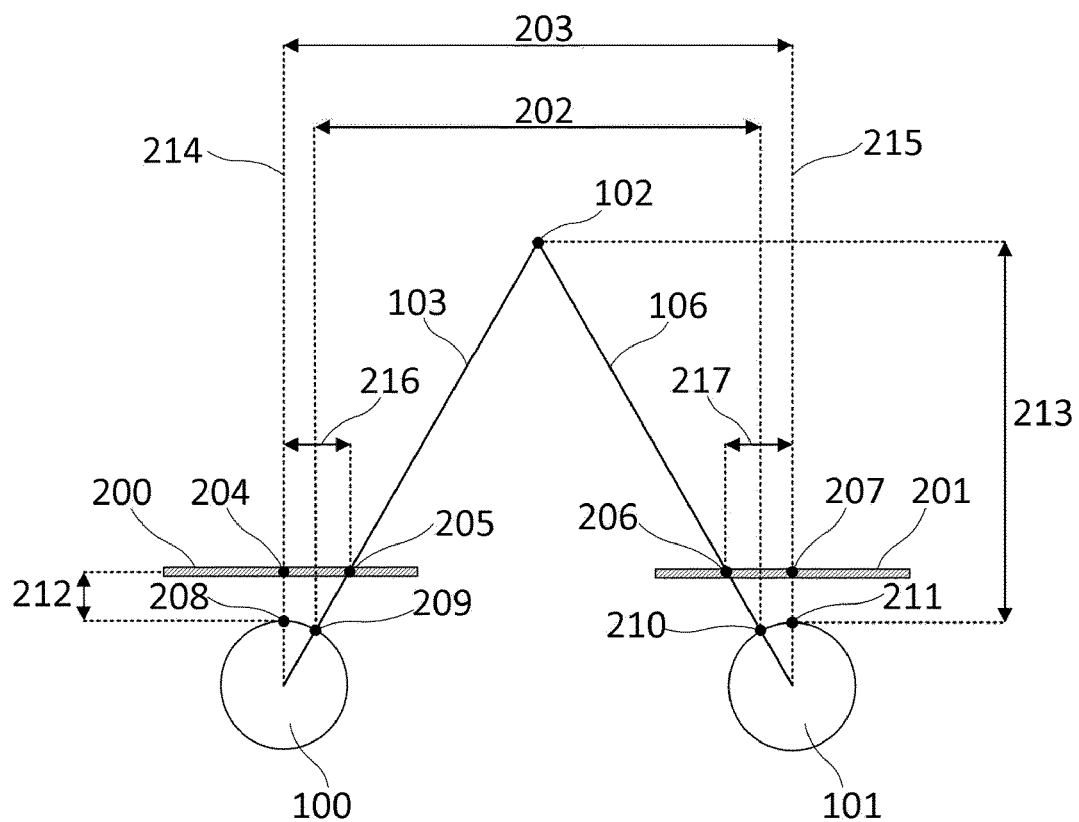
FIG. 2 graphically represents an ocular configuration similar to the one of FIG. 1 and various optometric elements/parameters related thereto.

FIG. 2 graphically represents an ocular configuration similar to the one of FIG. 1 and various optometric elements/parameters related thereto. In particular, this ocular configuration is shown with the eyes 100, 101 (from FIG. 1) in two different situations: a first situation of near fixation (similar to the one of FIG. 1) and a second situation of far fixation.

In relation to the mentioned situation of near fixation, the center of the pupil of the right eye 101 is in a position 210 on the visual axis 106 and the center of the pupil of the left eye 100 is in a position 209 on the visual axis 103, both axes 103, 106 according to a theoretical near fixation point 102. The distance 202 between said positions of the pupil centers 209, 210 is called near inter-pupillary distance 202.

With respect to the mentioned situation of far fixation, the center of the pupil of the right eye 101 is in a position 211 on a visual axis of far vision 215 and the center of the pupil of the left eye 100 is in a position 208 on a visual axis of far vision 214. The distance 203 between said positions of the pupil centers 208, 211 is called far inter-pupillary distance 203.

FIG. 2 also shows a progressive ophthalmic lens 201 for the right eye 101, and a progressive ophthalmic lens 200 for the left eye 100. These lenses 200, 201 may have a power for near vision and a power for far vision prescribed to the user. The prescription of these powers may have been performed through any known optometric technique.

FIG. 2 also shows a working distance 213 and a vertex distance 212. The working distance 213 corresponds to the distance between the eyes 100, 101 of the user and a working area 102 which is habitual/comfortable for the user (such as e.g. a reading distance). This working distance 213 may be one or another depending on whether a power for near vision prescribed to the user is considered or not.

The vertex distance 212 (for a given glasses frame) correspond to a distance between the front surface of the eye 100, 101 and the rear surface of the lens 200, 201 mounted on the glasses frame.

In FIG. 2, a near vision point 205 (intersection between the axis of near vision 103 and the lens 200) and a far vision point 204 (intersection between the axis of far vision 214 and the lens 200) for the left eye 100 are also shown. Similarly, a near vision point 206 (intersection between the axis of near vision 106 and the lens 201) and a far vision point 207 (intersection between the axis of far vision 215 and the lens 201) for the right eye 101 are shown.

Displacement 216 from the far vision point 204 to the near vision point 205 of the left lens 200 would be the inset 216 of the left lens 200, and displacement 217 from the far vision point 207 to the near vision point 206 of the right lens 201 would be the inset 217 of the right lens 201.

These concepts of near inter-pupillary distance 202, far inter-pupillary distance 203, vertex distance 212, working distance 213, and insets 216, 217 will be used in other parts of the description in the context of various examples.

Figure 3:
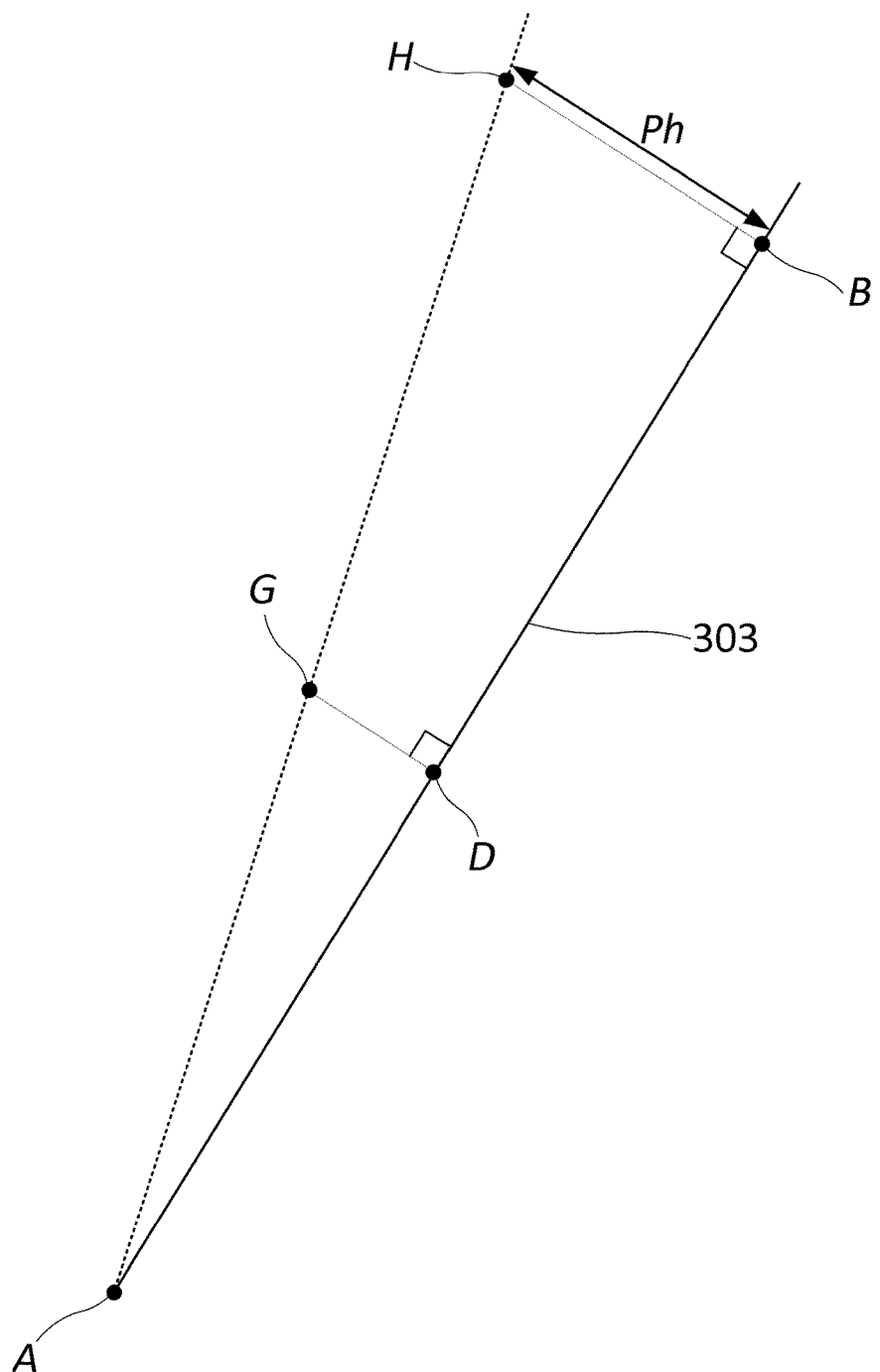
FIG. 3 shows a graphical representation of a mathematical model suitable for determining an inset for a progressive lens for a non-dominant eye, according to a first example.

FIG. 3 shows a graphical representation of a mathematical model suitable for determining an inset for a progressive ophthalmic lens for the non-dominant eye of a user, according to a first example.

This model is based on the representation of three main elements: a theoretical vision axis 303, a segment $\overline{AD}$ on said axis 303, and a segment $\overline{HB}$ perpendicular to said axis 303. The theoretical vision axis 303 is similar to the axis 103 of FIGS. 1-2 and may represent a standard vision axis (without associated phoria) for the dominant eye of the user. The segment $\overline{AD}$ may represent a vertex distance for a selected glasses frame. The segment $\overline{HB}$ may represent a measurement of phoria Ph (expressed in, for example, prism diopters) for the non-dominant eye of the user.

As shown in the figure, these three elements may define two right-angled triangles. A first right-angled triangle is defined by points A, D and G, wherein the segment $\overline{GD}$ is perpendicular to the vision axis 303 and, therefore, to the segment $\overline{AD}$. A second right-angled triangle is defined by points A, B and H, wherein the segment $\overline{HB}$ is perpendicular to the vision axis 303 and, therefore, to the segment $\overline{AB}$.

The point H may be derived from the concept of prism diopter, which may be defined as the unit that specifies the deviation produced by an ophthalmic prism. The prism diopter therefore represents a deviation of one centimeter on a flat surface situated one meter from the prism.

According to this definition of prism diopter, the segment $\overline{AB}$ may have a length of 1 meter (or 1.000 millimeters), and the segment $\overline{HB}$ may have a length substantially equal to the measurement of phoria Ph, which is expressed in centimeters in FIG. 3. Therefore, the length of the segment $\overline{HB}$ in millimeters may be substantially equal to Ph_mm=Ph×10 (it is multiplied by 10 to convert centimeters to millimeters).

According to trigonometric principles, the following equation has to be satisfied:

$$\overline{GD}/\overline{AD}=\overline{HB}/\overline{AB} \qquad \text{Formula 4}$$

wherein:
$\overline{GD}$ represents the length of the segment $\overline{GD}$ of the figure,
$\overline{AD}$ represents the length of the segment $\overline{AD}$ of the figure,
$\overline{HB}$ represents the length of the segment $\overline{HB}$ of the figure, and
$\overline{AB}$ represents the length of the segment $\overline{AB}$ of the figure.

Assuming that the length of $\overline{AD}$ may be equal to (approximately) 12 mm, because this is a widely accepted standard vertex distance, Formula 4 may be expressed as follows:

$$\overline{GD}/12=(Ph\times 10)/1000 \qquad \text{Formula 5}$$

From Formula 5, it may be derived that the length of the segment $\overline{GD}$ may be obtained according to the following formula:

$$\overline{GD} = \frac{Ph\times 10}{1000}\times 12 \qquad \text{Formula 6}$$

According to the previous definitions of phoria, prism diopter, working distance and inset, and taking into account that the axis 303 may represent a standard vision axis (without associated phoria) for a dominant eye, it may be understood that the length of $\overline{GD}$ is the deviation of the inset for the non-dominant eye with respect to the inset for the dominant eye.

Therefore, the inset for the lens of the non-dominant eye may be calculated according to the following formula:

$$\text{inset\_nondom} = \text{inset\_dom} - \frac{Ph\times 10}{1000}\times 12 \qquad \text{Formula 2}$$

wherein:
inset_nondom is the inset for the lens of the non-dominant eye,
inset_dom is the inset for the lens of the dominant eye, and
Ph is the value of phoria associated with the user (in centimeters).

The value of the measurement of phoria Ph may have a positive sign if it reflects exophoria, in which case the inset for the lens of the dominant eye inset_dom is greater than the inset for the lens of the non-dominant eye inset_nondom. The value of the measurement of phoria Ph may have negative sign if it reflects esophoria, in which case the inset for the lens of the dominant eye inset_dom is less than the inset for the lens of the non-dominant eye inset_nondom.

Referring again to FIG. 3, a person skilled in the art will understand that other formulas different from Formula 2 may be derived from the proposed mathematical model. For example, other distances $\overline{AD}$ different from 12 mm may be assumed, in which case formulas similar to Formula 2 but different therefrom could be obtained to determine the inset for the lens of the non-dominant eye.

It is also worth noting that the model illustrated by FIG. 3 may be interpreted as related to the left eye of the user and, therefore, suitable for obtaining the inset of the lens of the left eye as non-dominant eye. The skilled person will understand, however, that the same or similar principles described in relation to FIG. 3 may be applied to obtain a formula equivalent to Formula 2 for the right eye.

Figure 4:
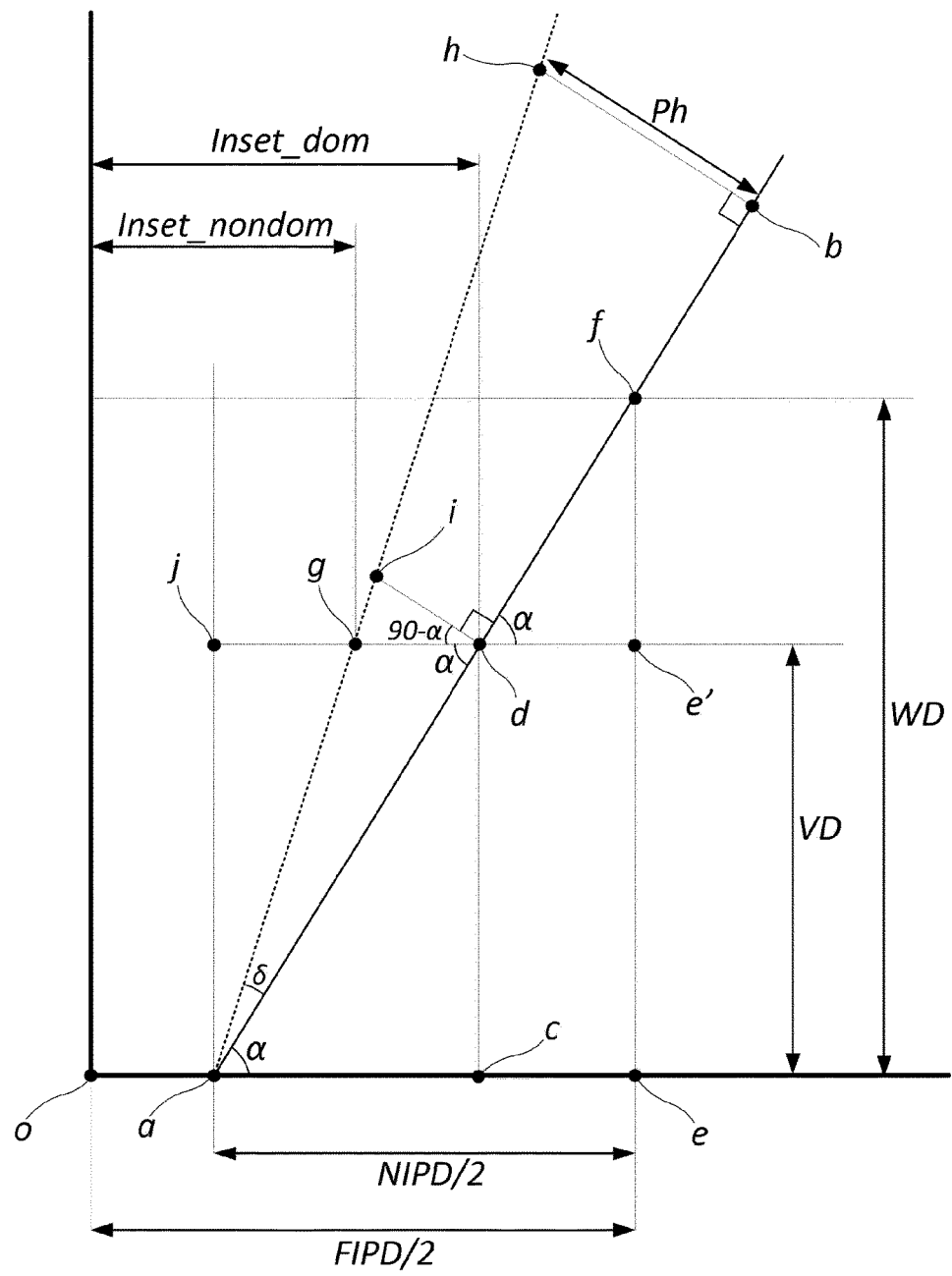
FIG. 4 shows a graphical representation of a mathematical model suitable for determining an inset for a progressive lens for a dominant eye and an inset for a progressive lens for a non-dominant eye, according to a second example.

FIG. 4 shows a graphical representation of a mathematical model suitable for determining an inset for the lens of the dominant eye of a user and an inset for the lens of the non-dominant eye of the user, according to a second example.

The model represented in this figure is similar to the one of FIG. 3, but in this case some additional variables are considered, such as e.g. near inter-pupillary distance NIPD and far inter-pupillary distance FIPD. Therefore, the following description in relation to FIG. 4 may refer to concepts/principles previously used in the description of FIG. 3.

According to the model of FIG. 4, the inset for the lens of the eye without associated phoria, i.e. the dominant eye (inset_dom) may be expressed by the following mathematical relationship:

$$\text{inset\_dom} = \overline{oa} + \overline{jd} = ((FIPD-NIPD)/2) + \overline{jd} \quad \text{Formula 8}$$

Furthermore, the distance $\overline{jd}$ may be expressed by the following mathematical relationship:

$$\overline{jd} = \overline{ae} - \overline{de'} = NIPD/2 - \overline{de'} \quad \text{Formula 9}$$

Taking into account the right-angled triangle formed by the segments $\overline{de'}$, $\overline{df}$ and $\overline{fe'}$, along with the definition of tangent, the distance $\overline{de'}$ may be expressed by the following mathematical relationship:

$$\overline{de'} = \overline{fe'}/\tan(\alpha) = (WD-VD)/\tan(\alpha) \quad \text{Formula 10}$$

Taking into account the Formula 9 and Formula 10, the distance $\overline{jd}$ may be expressed by the following mathematical relationship:

$$\overline{jd} = NIPD/2 - (WD-VD)/\tan(\alpha) \quad \text{Formula 11}$$

Taking into account the right-angled triangle formed by the segments $\overline{ae}$, $\overline{af}$ and $\overline{fe}$, along with the definition of tangent, the tangent of α may be expressed by the following mathematical relationship:

$$\tan(\alpha) = \overline{fe}/\overline{ae} = WD/(NIPD/2) \quad \text{Formula 12}$$

Taking into account the Formula 11 and Formula 12, the distance $\overline{jd}$ may be expressed by the following mathematical relationship:

$$\overline{jd} = NIPD/2 - (WD-VD)/(WD/(NIPD/2)) \quad \text{Formula 13}$$

Taking into account the Formula 8 and Formula 13, the inset for the lens of the dominant eye (inset_dom) may be determined by the following mathematical relationship:

$$\text{inset\_dom} = \frac{FIPD - NIPD}{2} + \frac{NIPD}{2} - \frac{WD - VD}{WD/(NIPD/2)} \quad \text{Formula 1}$$

$$\text{inset\_dom} = \frac{FIPD}{2} - \frac{NIPD}{2} + \frac{NIPD}{2} - \frac{WD - VD}{WD/(NIPD/2)}$$

$$\text{inset\_dom} = \frac{FIPD}{2} - \frac{WD - VD}{WD/(NIPD/2)}$$

The inset for the lens of the eye with associated phoria, i.e. the non-dominant eye (inset_nondom) may be expressed by the following mathematical relationship:

$$\text{inset\_nondom} = \overline{oa} + \overline{jg} = ((FIPD-NIPD)/2) + \overline{jg} \quad \text{Formula 14}$$

The distance $\overline{jg}$ may be expressed by the following mathematical relationship:

$$\overline{jg} = \overline{jd} - \overline{gd} \quad \text{Formula 15}$$

Taking into account the Formula 8, the distance $\overline{jg}$ may be expressed by the following mathematical relationship:

$$\overline{jd} = \text{inset\_dom} - (FIPD-NIPD)/2 \quad \text{Formula 16}$$

Taking into account the Formula 15 and Formula 16, the distance $\overline{jg}$ may be expressed by the following mathematical relationship:

$$\overline{jg} = \text{inset\_dom} - (FIPD-NIPD)/2 - \overline{gd} \quad \text{Formula 17}$$

Taking into account the right-angled triangle formed by the segments $\overline{gd}$, $\overline{gi}$ and $\overline{id}$, along with the definition of cosine, the distance $\overline{gd}$ may be expressed by the following mathematical relationship:

$$\overline{gd} = id/\cos(90-\alpha) \quad \text{Formula 18}$$

Taking into account the right-angled triangle formed by the segments $\overline{ai}$, $\overline{ad}$ and $\overline{id}$, along with the definition of tangent, the tangent of δ may be expressed by the following mathematical relationship:

$$\tan(\delta) = \overline{id}/\overline{ad} \quad \text{Formula 19}$$

Taking into account the right-angled triangle formed by the segments $\overline{ah}$, $\overline{ab}$ and $\overline{hb}$, along with the definition of tangent, the tangent of δ may also be expressed by the following mathematical relationship:

$$\tan(\delta) = \overline{hb}/\overline{ab} = Ph/\overline{ab} \quad \text{Formula 20}$$

Taking into account the Formula 19 and Formula 20, the following equation may be established:

$$\overline{id}/\overline{ad} = Ph/\overline{ab} \quad \text{Formula 21}$$

Taking into account the Formula 21 and that the distance $\overline{ab}$ may be equal to 1000 mm (according to the definition of prism diopter provided in the description of FIG. 3), the distance $\overline{id}$ may be expressed by the following mathematical relationship:

$$\overline{id} = Ph \times \overline{ad}/\overline{ab} = Ph \times \overline{ad}/1000 \quad \text{Formula 22}$$

Taking into account the right-angled triangle formed by the segments $\overline{ac}$, $\overline{ad}$ and $\overline{cd}$, along with the definition of sinus, the distance $\overline{ad}$ may be expressed by the following mathematical relationship:

$$\overline{ad} = \overline{cd}/\sin(\alpha) = VD/\sin(\alpha) \quad \text{Formula 23}$$

Taking into account the Formula 22 and Formula 23, the distance $\overline{id}$ may be expressed by the following mathematical relationship:

$$\overline{id} = Ph \times (VD/\sin(\alpha))/1000 \quad \text{Formula 24}$$

Taking into account the Formula 18 and Formula 24, the distance $\overline{gd}$ may be expressed by the following mathematical relationship:

$$\overline{gd} = (Ph \times (VD/\sin(\alpha))/1000)/\cos(90-\alpha) \quad \text{Formula 25}$$

Taking into account the Formula 12, the angle α may be expressed by the following mathematical relationship:

$$\alpha = \arctan(WD/(NIPD/2)) \quad \text{Formula 26}$$

Taking into account the Formula 25 and Formula 26, the distance $\overline{gd}$ may be expressed by the following mathematical relationship:

$$\overline{gd} = \frac{Ph \times (VD/\sin(\arctan(WD/(NIPD/2))))/1000}{\cos(90 - \arctan(WD/(NIPD/2)))} \quad \text{Formula 27}$$

Taking into account the Formula 17 and Formula 27, the distance $\overline{jg}$ may be expressed by the following mathematical relationship:

$$\overline{jg} = \text{inset\_dom} - \frac{(FIPD - NIPD)}{2} - \frac{\frac{Ph \times (VD/\sin(\arctan(WD/(NIPD/2))))}{1000}}{\cos(90 - \arctan(WD/(NIPD/2)))}$$

Formula 28

Taking into account the Formula 14 and Formula 28, the inset for the lens of the non-dominant eye (inset_nondom) may be determined by the following mathematical relationship:

$$\text{inset\_nondom} =$$

Formula 3

$$\frac{(FIPD - NIPD)}{2} + \text{inset\_dom} - \frac{(FIPD - NIPD)}{2} - \frac{\frac{Ph \times (VD/\sin(\arctan(WD/(NIPD/2))))}{1000}}{\cos(90 - \arctan(WD/(NIPD/2)))}$$

$$\text{inset\_nondom} = \text{inset\_dom} - \frac{\frac{Ph \times (VD/\sin(\arctg(WD/(NIPD/2))))}{1000}}{\cos(90 - \arctg(WD/(NIPD/2)))}$$

Referring again to FIG. 4, one skilled in the art will understand that other formulas different from Formulas 1 and 3 may be derived from the proposed mathematical model. For example, other trigonometric relations different from those used in the previous descriptions may be employed, in which case formulas similar to Formulas 1 and 3 but different therefrom could be obtained to determine the inset for the lens of the dominant eye and the inset for the lens of the dominant eye, respectively.

It is also worth noting that the model illustrated by FIG. 4 may be interpreted as relating to the left eye of the user and, therefore, suitable for obtaining the inset of the lens of the left eye, either the dominant eye or the non-dominant eye. The skilled person will understand, however, that the same or similar principles described in relation to FIG. 4 may be applied to obtain formulas equivalent to Formulas 1 and 3 for the right eye.

Models of FIGS. 3 and 4 may allow thus obtaining different formulas for obtaining an inset for the lens of the dominant eye of a user and an inset for the lens of the non-dominant eye of the same user. It has also been described that the inset for the lens of the dominant eye may be a standard fixed value (for example 2.5 mm).

These different ways of obtaining the insets may be used in different proposed design methods, mainly based on calculating or determining the inset for the lens of the non-dominant eye depending on the inset for the lens of the dominant eye and at least one measurement of phoria associated with the non-dominant eye of the user. It has been experimentally verified that this approach may improve the adaptation of the user to the lenses, because the user may not have to move his or her fixation with excessive demand for fusional reserves.

These advantages may also be attributed to any methods of manufacturing lenses that use any one of the described design methods, and to any lenses designed according to any of said design methods and/or manufactured according to any of said manufacturing methods.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments that have been described. The numerical signs relating to the drawings and placed between parentheses in a claim are only aimed at increasing the understanding of the claim and shall not be interpreted as limiting the scope of protection of the claim. The scope of the present invention should not be limited by particular embodiments, but should be determined only by a fair reading of the claims that follow.

Further, although the embodiments of the invention described with reference to the drawings comprise computer systems and methods performed by computer systems, the invention also extends to computer programs, particularly to computer programs on or in a carrier, adapted for putting the invention into practice. The program may be in the form of source code, object code, or an intermediate code between source code and object code, such as in partially compiled form, or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means.

When the program is embodied in a signal that may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

Furthermore, the invention may also be implemented by computer systems such as personal computers, servers, a network of computers, laptops, tablets or any other programmable device or computer processor. Further or alternatively, programmable electronic devices may also be used, such as programmable logic controllers (ASICs, FPGAs, PLCs, etc.).

Therefore, the invention may be implemented both in hardware and in software or in firmware, or any combination thereof.

The invention claimed is:

1. A method of designing at least one progressive ophthalmic lens for a user having a dominant eye and a non-dominant eye, the method comprising:
   determining a first inset for a lens for the dominant eye;
   determining a measurement of phoria of the user;
   determining a second inset for a lens for the non-dominant eye depending on the first inset and on the measurement of phoria; and
   designing the lens for the non-dominant eye according to the second inset.

2. The design method according to claim 1, wherein determining the first inset for the lens for the dominant eye comprises determining the first inset with a fixed value of between 2 and 3 mm.

3. The design method according to claim 1, further comprising:
   determining a measurement of far inter-pupillary distance for the user;

determining a measurement of near inter-pupillary distance for the user;

determining a measurement of working distance depending on a power for near vision prescribed to the user; and determining a measurement of vertex distance depending on a glasses frame selected for the user; and wherein the determining the first inset for the lens for the dominant eye comprises determining the first inset depending on the measurements of far inter-pupillary distance, near inter-pupillary distance, working distance and vertex distance.

4. The design method according to claim 3, wherein the determining the first inset depending on the measurements of far inter-pupillary distance, near inter-pupillary distance, working distance and vertex distance comprises determining the first inset according to the following formula:

$$\text{inset\_dom} = \frac{FIPD}{2} - \frac{WD - VD}{WD/(NIPD/2)} \quad \text{Formula 1}$$

wherein:
inset_dom is the first inset for the lens of the dominant eye,
FIPD is the measurement of the far inter-pupillary distance,
NIPD is the measurement of the near inter-pupillary distance,
WD is the measurement of the working distance depending on the prescribed power for near vision, and
VD is the measurement of the vertex distance.

5. The design method according to claim 1, wherein the determining the second inset for the lens for the non-dominant eye comprises determining the second inset according to the following formula:

$$\text{inset\_nondom} = \text{inset\_dom} - \frac{Ph \times 10}{1000} \times 12 \quad \text{Formula 2}$$

wherein:
inset_nondom is the second inset for the lens of the non-dominant eye of the user,
inset_dom is the first inset for the lens of the dominant eye of the user, and
Ph is the measurement of phoria of the user.

6. The design method according to claim 1, further comprising:
determining a measurement of near inter-pupillary distance of the user;
determining a measurement of working distance depending on a power for near vision prescribed to the user; and
determining a measurement of vertex distance depending on a glasses frame selected for the user; and wherein the determining the second inset for the lens for the non-dominant eye comprises determining the second inset depending on the first inset, the measurement of phoria and the measurements of near inter-pupillary distance, working distance and vertex distance.

7. The design method according to claim 6, wherein the determining the second inset depending on the first inset, the measurement of phoria and the measurements of near inter-pupillary distance, working distance and vertex distance comprises determining the second inset according to the following formula:

$$\text{inset\_nondom} = \text{inset\_dom} - \frac{Ph \times (VD/\sin(\arctg(WD/(NIPD/2))))}{1000} \quad \text{Formula 3}$$
$$\cos(90 - \arctg(WD/(NIPD/2)))$$

wherein:
inset_nondom is the second inset for the lens of the non-dominant eye,
inset_dom is the first inset for the lens of the dominant eye,
NIPD is the measurement of the near inter-pupillary distance,
WD is the measurement of the working distance depending on the prescribed power for near vision,
VD is the measurement of the vertex distance, and
Ph is the measurement of phoria of the user.

8. The design method according to claim 1, further comprising:
designing the lens for the dominant eye according to the first inset.

9. A method of manufacturing at least one progressive ophthalmic lens, the method comprising:
designing the at least one progressive ophthalmic lens by performing a design method according to claim 1; and
manufacturing the at least one progressive ophthalmic lens according to the result of designing the at least one progressive ophthalmic lens.

10. A computer system comprising a nonvolatile memory and a processor, wherein the memory stores computer program instructions executable by the processor, the instructions comprising logic for executing a design method according to claim 1.

11. A computer program product stored on nonvolatile memory and comprising program instructions that cause a system to execute a design method according to claim 1.

12. The design method according to claim 2, wherein the determining the second inset for the lens for the non-dominant eye comprises determining the second inset according to the following formula:

$$\text{inset\_nondom} = \text{inset\_dom} - \frac{Ph \times 10}{1000} \times 12 \quad \text{Formula 2}$$

wherein:
inset_nondom is the second inset for the lens of the non-dominant eye of the user,
inset_dom is the first inset for the lens of the dominant eye of the user, and
Ph is the measurement of phoria of the user.

13. The design method according to claim 3, wherein the determining the second inset for the lens for the non-dominant eye comprises determining the second inset according to the following formula:

$$\text{inset\_nondom} = \text{inset\_dom} - \frac{Ph \times 10}{1000} \times 12 \quad \text{Formula 2}$$

wherein:
- inset_nondom is the second inset for the lens of the non-dominant eye of the user,
- inset_dom is the first inset for the lens of the dominant eye of the user, and
- Ph is the measurement of phoria of the user.

14. The design method according to claim 4, wherein the determining the second inset for the lens for the non-dominant eye comprises determining the second inset according to the following formula:

$$\text{inset\_nondom} = \text{inset\_dom} - \frac{Ph \times 10}{1000} \times 12 \qquad \text{Formula 2}$$

wherein:
- inset_nondom is the second inset for the lens of the non-dominant eye of the user,
- inset_dom is the first inset for the lens of the dominant eye of the user, and
- Ph is the measurement of phoria of the user.

15. The design method according to claim 2, further comprising:
- determining a measurement of near inter-pupillary distance of the user;
- determining a measurement of working distance depending on a power for near vision prescribed to the user; and
- determining a measurement of vertex distance depending on a glasses frame selected for the user; and wherein
- the determining the second inset for the lens for the non-dominant eye comprises determining the second inset depending on the first inset, the measurement of phoria and the measurements of near inter-pupillary distance, working distance and vertex distance.

16. The design method according to claim 3, further comprising:
- determining a measurement of near inter-pupillary distance of the user;
- determining a measurement of working distance depending on a power for near vision prescribed to the user; and
- determining a measurement of vertex distance depending on a glasses frame selected for the user; and wherein
- the determining the second inset for the lens for the non-dominant eye comprises determining the second inset depending on the first inset, the measurement of phoria and said measurements of near inter-pupillary distance, working distance and vertex distance.

17. The design method according to claim 4, further comprising:
- determining a measurement of near inter-pupillary distance of the user;
- determining a measurement of working distance depending on a power for near vision prescribed to the user; and
- determining a measurement of vertex distance depending on a glasses frame selected for the user; and wherein
- the determining the second inset for the lens for the non-dominant eye comprises determining the second inset depending on the first inset, the measurement of phoria and said measurements of near inter-pupillary distance, working distance and vertex distance.

\* \* \* \* \*